United States Patent
Matsuo et al.

(10) Patent No.: US 6,984,731 B2
(45) Date of Patent: Jan. 10, 2006

(54) PROCESS FOR MANUFACTURING CELLULOSE ACETATE

(75) Inventors: Shunichi Matsuo, Tokyo (JP); Takatsugu Takamura, Saitama-ken (JP)

(73) Assignee: Nihon Zaikei Kabushiki Kaisha, Tokyo (JP)

( * ) Notice: Subject to any disclaimer, the term of this patent is extended or adjusted under 35 U.S.C. 154(b) by 4 days.

(21) Appl. No.: 10/439,809

(22) Filed: May 16, 2003

(65) Prior Publication Data

US 2004/0002598 A1 Jan. 1, 2004

(30) Foreign Application Priority Data

Jun. 26, 2002 (JP) .......................... 2002-186476

(51) Int. Cl.
C08B 3/06 (2006.01)
C07H 1/00 (2006.01)
C07H 1/06 (2006.01)

(52) U.S. Cl. .................. 536/69; 536/124; 536/128
(58) Field of Classification Search .................. 536/69, 536/124, 128
See application file for complete search history.

(56) References Cited

U.S. PATENT DOCUMENTS

| | | |
|---|---|---|
| 1,522,618 A | 1/1925 | Ditman |
| 4,306,060 A | 12/1981 | Ikemoto |
| 4,520,105 A | 5/1985 | Sinner et al. |
| 5,371,207 A * | 12/1994 | Zhuang ................ 536/58 |
| 5,658,765 A | 8/1997 | Noguchi et al. |
| 6,228,213 B1 * | 5/2001 | Hanna et al. .............. 162/18 |
| 6,352,644 B1 | 3/2002 | Clifford et al. |

FOREIGN PATENT DOCUMENTS

| | | | |
|---|---|---|---|
| CN | 1340651 A | * | 3/2002 |
| EP | 0 626 391 A1 | | 11/1994 |
| EP | 1 205 598 A1 | | 5/2002 |
| JP | 2000-212201 | | 8/2000 |
| JP | 2000-212202 | | 8/2000 |
| JP | 2000-333692 | | 12/2000 |
| JP | 2001-205070 | | 7/2001 |

* cited by examiner

Primary Examiner—James D. Wilson
Assistant Examiner—Everett White
(74) Attorney, Agent, or Firm—Knobbe Martens Olson & Bear, LLP

(57) ABSTRACT

The invention provides a process for manufacturing at low cost cellulose acetate, which is useful as a biodegradable plastic, using corncob meal which has hitherto been thrown away as a raw material. More specifically, the invention provides a process for manufacturing cellulose acetate, which comprises the steps of: steaming corncob meal at a temperature of 150 to 250° C. and a pressure of 20 to 29 MPa; filtering the steamed corncob meal to obtain a solid product; and dehydrating and acetylating by adding acetic anhydride and sulfuric acid to the solid product. The steaming is preferably carried out by using a pressure vessel and the filtering is preferably carried out by using a filtering device.

19 Claims, 1 Drawing Sheet

PROCESS FOR MANUFACTURING CELLULOSE ACETATE

CROSS-REFERENCE TO RELATED APPLICATION

This patent application claims priority to Japanese Patent Application No. 2002-186476 which is incorporated herein by reference.

BACKGROUND OF THE INVENTION

1. Field of the Invention

The present invention relates to a process for manufacturing cellulose acetate, which is useful as a biodegradable plastic and is made from corncob meal.

2. Description of the Related Art

Biodegradable plastic is a plastic, which, like any ordinary plastic, exhibits excellent functions when in use, but which is quickly decomposed by microorganisms in a natural environment (for example, in the soil) after use and eventually becomes organic components of earth, water and carbon dioxide, and is drawing attention in connection with the current problem of waste, etc.

Various kinds of biodegradable plastic products have been publicized. Examples of such products include polylactic acids produced by dehydration and polymerization from lactic acid obtained by fermenting starch of corn, potatoes, etc. with lactobacilli. Such products are used for an agricultural multi-film, a compost bag, etc. However, prices of raw materials and processing costs for products are high, and these products are not necessarily rational in consideration of foodstuff situations in the future. Polycaprolactone, which is given as another example of a biodegradable plastic, is also so expensive that it is difficult to use polycaplolactone as an agricultural material, etc., and use is limited to medical materials, etc., although polycaplolactone may be satisfactory in physical properties as a plastic and biodegradability.

Moreover, a plastic obtained merely by kneading corn starch with polyethylene is being sold as a biodegradable plastic. This plastic, however, is not a biodegradable plastic in the true sense of the word, since it has become clear that, although its constituent, which is derived from natural matter, such as starch, may be biodegradable, polyethylene does not undergo any change (decomposition). Such a product is being driven out of the market despite its low price.

Thus, spreading of the biodegradable plastics, which have been heretofore known, has been slow because of their unsatisfactory performance, or because they require a complicated process for manufacture and their prices are high. The demand for biodegradable plastic products is, however, expected to increase more and more in the future for protection of the global environment, and accordingly, there is a desire for the development of products having higher performance and lower costs. Under these circumstances, studies are being performed for a biodegradable plastic composed mainly of cellulose, which plants contain in a large quantity, or a derivative thereof. However, a high cost of manufacture of this biodegradable plastic is a problem, as is the case with other biodegradable plastics.

On the other hand, the majority of a corncob is composed of cellulose (lignocellulose and hemicellulose). Corncob meal, which is obtained by drying and crushing corncobs, is used as a fungal bed for growing mushrooms, an abrasive for pulse, a nest building material for animals, etc., but very little as an industrial material. The greater part of the corncobs produced is thrown away as waste. Incineration is a main method for waste disposal, thus, there are a lot of problems with waste disposal including degradation of the environment. Study is, therefore, under way for the effective use of corncobs.

When corncobs are used as a raw material for manufacturing a biodegradable plastic consisting mainly of cellulose or a derivative thereof, etc., the cost of the raw material is zero, as hardly any labor is required for gathering the raw material, etc., and costs that have hitherto been borne by agricultural producers for waste disposal are no longer incurred. Accordingly, a biodegradable plastic made from corncobs is considered to be highly price-competitive, compared to other biodegradable plastics.

However, despite having the features mentioned, there has not been developed any biodegradable plastic consisting mainly of cellulose or a derivative thereof, etc. made from corncobs. A possible reason for this is a high cost of esterification, etc., since it is difficult to obtain cellulose (pulp of high quality) by separating lignin from lignocelluloses of which corncobs mainly consist. The separation of lignin from lignocelluloses requires a lot of steps, i.e. grinding corncobs in a stone mill, boiling with alkali and applying a sulfurous acid treatment.

SUMMARY OF THE INVENTION

The invention solves the problems as stated above and provides an inexpensive process for manufacturing cellulose acetate that is useful as a biodegradable plastic by using as a raw material a corncob meal which has hitherto been thrown away. Moreover, the present invention provides a process for manufacturing xyloligosaccharides, which are useful as sweetening agents, from a by-product occurring in above manufacture of cellulose acetate.

Specifically, the present invention provides a process for manufacturing cellulose acetate, which comprises the steps of: steaming a corncob meal at a temperature of 150 to 250° C. and a pressure of 20 to 29 MPa; filtering the steamed corncob meal to obtain a solid product; and dehydrating and acetylating by adding acetic anhydride and sulfuric acid to the solid product.

DETAILED DESCRIPTION OF THE PREFERRED EMBODIMENTS

Figure 1:
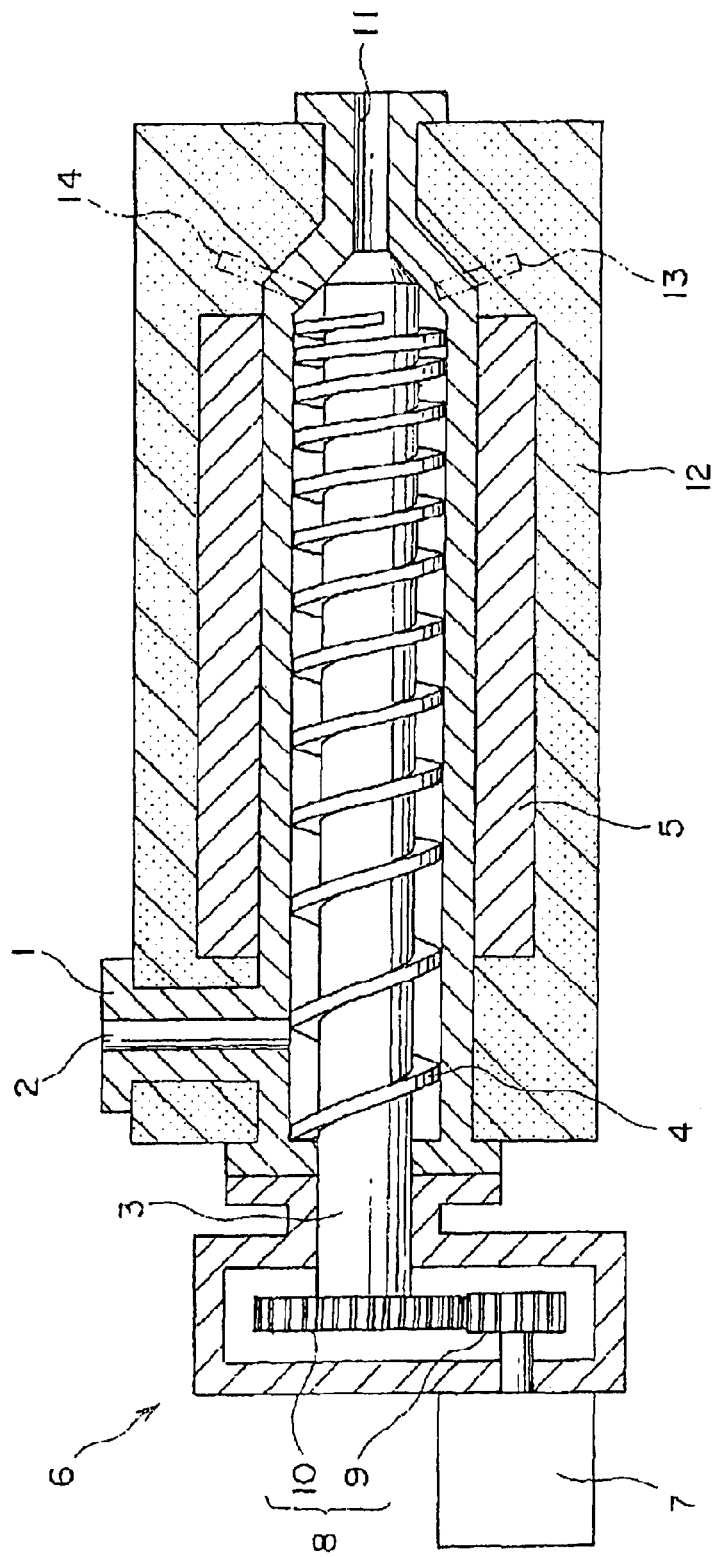
FIG. 1 is a partial sectional view of an extruder having a pressure-sealed cylinder as an example of a pressure vessel for carrying out the steaming treatment according to the present invention.

The process for manufacturing cellulose acetate and xyloligosaccharides of the present invention is characterized by steaming corncob meal at a temperature of 150 to 250° C. and a pressure of 20 to 29 MPa (which may hereinafter be referred to as steaming treatment), then separating a solid product from a filtrate.

The steaming treatment according to the present invention is a process of adding water to the corncob meal (a powder obtained by drying and crushing corncobs) and steaming the mixture at 150 to 250° C. and 20 to 29 MPa, which are defining the conditions for the sub-critical state (immediately before the supercritical). The steaming treatment according to the present invention makes it possible to carry out in a simple and convenient way the separation of lignin from lignocelluloses which has hitherto required a lot of steps.

The steaming treatment requires a temperature of 150 to 250° C. and a pressure of 20 to 29 MPa, and preferably a temperature of 180 to 200° C. and a pressure of 25 to 28 MPa. The amount of water added is preferably 10 to 1000 parts by weight and more preferably 50 to 100 parts by weight, relative to 100 parts by weight of corncob meal. The steaming treatment is preferably carried out for 10 to 30 minutes, and more preferably for 15 to 20 minutes.

Moreover, in the steaming treatment, a sulfurous acid compound may be added to the corncob meal. The addition of the sulfurous acid compound to the corncob meal makes it possible to shorten the time for the steaming treatment. Examples of the sulfurous acid compound include sodium or calcium sulfite. The amount of the sulfurous acid compound which is added is preferably 1 to 10 parts by weight, and more preferably 2 to 5 parts by weight, for 100 parts by weight of corncob meal.

The steaming treatment is preferably carried out by using a pressure vessel, and is particularly preferably carried out by an extruder having a pressure-sealed cylinder as shown in FIG. 1. FIG. 1 is a partial sectional view of an extruder having a pressure-sealed cylinder, which is an example of a pressure vessel for carrying out the steaming treatment according to the present invention. The extruder is composed of: a cylinder 1 having a material input port 2 at its base; a screw 3 having a spiral flight 4 for kneading (steaming) and extruding toward its distal end the corncob meal and water (which may hereinafter be referred to simply as the materials), which were inputted through the material input port 2; a heater 5 for heating the cylinder 1; drive means 6 including a motor 7 connected to a power source (not shown) for rotating the screw 3 and a reduction gear 8 having a prime gear 9 and a driven gear 10; a discharging port 11 for discharging a steamed and extruded product; a heat insulating material 12 covering the cylinder 1 and the heater 5, etc. A pump (not shown) is connected with the material input port 2 for feeding the materials into the cylinder 1 through the material input port 2. A pitch of the spiral flight 4 of the screw 3 shortens as the spiral flight 4 approaches the discharging port 11. Moreover, the cylinder 1 has a temperature sensor 13 and a pressure sensor 14 installed near the distal end of the screw 3.

The steaming treatment is carried out by the extruder, which is shown in FIG. 1, in accordance with the following sequence. The materials are inputted by the unillustrated pump into the cylinder 1 through its material input port 2 and the internal temperature of the cylinder 1 is regulated to a target temperature by the heater 5. As viewed from the motor 7, a rotary shaft of the motor 7 rotated clockwise to rotate the primer gear 9 clockwise, the driven gear 10 counterclockwise and the screw 3 counterclockwise, thus boiling the corncob meal while extruding the corncob meal toward the discharging port 11. Since the pitch of the spiral flight 4 of the screw 3 shortens toward the discharging port 11, the corncob meal is compressed and subjected to a specific pressure as it approaches the discharging port 11. The corncob meal, for which the steaming treatment has been completed, is extruded through the discharging port 11.

While, in the present embodiment, the temperature sensor 13 and the pressure sensor 14 are installed in the cylinder 1 near the distal end of the screw 3, it is sufficient for an installation position of the temperature sensor 13 to be further to the distal end side of the screw 3 than a middle portion, with respect to the axial direction, of the cylinder 1. It is sufficient for an installation position of the pressure sensor 14 to be in a space, which is a distal-end of the screw 3 of the cylinder 1.

When the steaming treatment is carried out by the extruder shown in FIG. 1, it is necessary for the temperature and pressure determined by the temperature sensor 13 and the pressure sensor 14 to fall within the ranges of 150 to 250° C. and 20 to 29 MPa, respectively.

Moreover, it is also suitable to employ a process in which two or more units of extruder shown in FIG. 1 are connected in series for steaming treatment, i.e. a process in which a mixture of corncob meal and water steamed in a first extruder and extruded through a discharging port 11 thereof is directly inputted into the material input port 2 of a second extruder for further steaming. When two or more units of extruder shown in FIG. 1 are connected in series for the steaming treatment, the steaming conditions in the extruders may be the same, or differ from one another as long as the steaming conditions for the last connected extruder satisfy the conditions of the temperature of 150 to 250° C. and the pressure of 20 to 29 MPa. In the case which the steaming conditions differ from one extruder to another, it is preferable for the temperature and pressure to rise from the first extruder to the last connected extruder.

The steaming treatment of the corncob meal as described above obtains a mixture of polyphenol (formed by a change from the lignin) and cellulose which are formed by the decomposition of lignocelluloses, and of soluble hemicelluloses (hereinafter referred to as soluble xylan). The filtration treatment of the mixture enables it to be separated into cellulose (pulp of high quality) as a solid and a mixed solution of polyphenol and soluble xylan. The filtration treatment is preferably carried out by a filtering device.

The cellulose obtained by separating lignin with the filtration treatment is crystallized due to the formation of hydrogen bonds by the hydroxyl groups and is insoluble in both water and any solvent. Therefore, dehydrating and acetylating is carried out as described below for converting a portion of hydroxyl groups in the molecule to acetate groups to obtain a plasticized cellulose acetate, which is soluble in both water and a solvent. The dehydrating and acetylating is preferably carried out in a pressure vessel equipped with a stirrer.

The dehydrating and acetylating is intended for reacting cellulose with acetic anhydride and sulfuric acid to substitute acetate groups for the hydroxyl groups, causing the formation of hydrogen bonds in the cellulose, and is expressed by reaction formulae (1) and (2) below when n is the degree of polymerization and m is the degree of substitution.

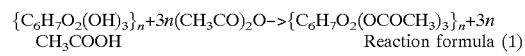
$\{C_6H_7O_2(OH)_3\}_n + 3n(CH_3CO)_2O \rightarrow \{C_6H_7O_2(OCOCH_3)_3\}_n + 3n\ CH_3COOH$  Reaction formula (1)

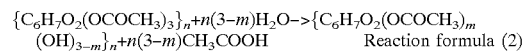
$\{C_6H_7O_2(OCOCH_3)_3\}_n + n(3-m)H_2O \rightarrow \{C_6H_7O_2(OCOCH_3)_m(OH)_{3-m}\}_n + n(3-m)CH_3COOH$  Reaction formula (2)

Reaction formula (1) shows that the reaction of cellulose and acetic anhydride produces cellulose acetate and acetic acid with the complete substitution of acetate groups. On the other hand, reaction formula (2) shows that the reaction of cellulose acetate produced in accordance with reaction formula (1) and water produces cellulose acetate having a degree of substitution m and acetic acid. The acetic acid produced in accordance with reaction formulae (1) and (2) can be reused.

The dehydrating and acetylating can be carried out in accordance with the following sequence. After the solid (cellulose) obtained by the filtration treatment is washed with water to remove alkali therefrom, sulfuric acid and acetic anhydride are added to and reacted with the obtained solid, acetic acid is removed (collected) from the resulting reaction product by a dehydrator, and is dried. The above procedure obtains cellulose acetate having an acetylation degree of 51 to 61.

The amount of sulfuric acid which is added is preferably 1 to 10 parts by weight and more preferably 3 to 5 parts by weight relative to 100 parts by weight of dry cellulose. The amount of acetic anhydride which is added is preferably 1 to 20 parts by weight and more preferably 5 to 10 parts by weight, relative to 100 parts by weight of dry cellulose. Moreover, acetic acid can be preferably added, and the amount thereof added is preferably 1 to 10 parts by weight and more preferably 3 to 5 parts by weight relative to 100 parts by weight of cellulose.

The dehydration and acetylation is preferably carried out under a pressure of 5 to 15 MPa, and more preferably 8 to 10 Mpa. The temperature for the dehydration and acetylation is preferably from 60 to 100° C. and more preferably from 70 to 90° C. The stirring speed for the dehydration and acetylation is preferably from 30 to 100 rpm and more preferably from 40 to 60 rpm. The duration of the dehydration and acetylation is preferably from 15 to 30 hours and more preferably from 20 to 24 hours.

While cellulose acetate is a biodegradable plastic itself, it is also possible to use cellulose acetate as a base and knead various kinds of materials (for example, corn starch and polylactic acid) therein to make biodegradable plastics of different properties.

On the other hand, soluble xylan obtained by the filtration treatment becomes xyloligosaccharides by hydrolytic treating (enzyme treatment) xylanase. The enzyme treatment can be carried out in the following sequence: xylanase is added to and reacted with the filtrate from which the solid was removed by the filtering device, in a reaction vessel equipped with a stirrer and having a temperature holding mechanism; any suspended matter is removed from the resulting reaction product by the filtering device and is dried. Xyloligosaccharides are obtained by the above sequence.

The amount of xylanase added in the enzyme treatment is preferably from 0.1 to 5 parts by weight and more preferably from 0.5 to 2 parts by weight relative to 100 parts by weight of filtrate. The enzyme treatment is preferably carried out at a pH of 3 to 8 and more preferably at a pH of 4 to 6. Moreover, the temperature for the treatment is preferably from 30 to 50° C. and more preferably from 40 to 45° C. The stirring speed is preferably from 60 to 200 rpm and more preferably from 100 to 150 rpm. The duration of the treatment is preferably from 15 to 30 hours and is more preferably from 20 to 24 hours.

While the enzyme treatment converts soluble xylan into xyloligosaccharides (sweetening agents), the soluble xylan by-product and this step can be omitted without the process for manufacturing a biodegradable plastic, but the addition of the step makes it possible to achieve an outstanding increase in the efficiency of use of raw materials, reduction of wastes, and also the auxiliary production of useful products. In other words, the enzyme treatment can lower the cost of manufacture of cellulose acetate. Incidentally, xyloligosaccharides are used in various kinds of food owing to their effect of preventing tooth decay and establishing a good balance of coliform bacteria for health promotion, and demand for xyloligosaccharides is expected to increase greatly in the future.

EXAMPLES

The invention will now be described more specifically by way of examples, though the invention is not limited to these examples.

Example 1

The steaming of a corncob meal was carried out by four serially connected units of pressure-sealed extruder as shown in FIG. 1. The four serially connected extruders included a first extruder with a discharging port 11 thereof connected to a material input port 2 of a second extruder, and the rest were likewise connected until a fourth extruder, so that a kneaded mixture steamed in the first extruder could be inputted into the cylinder 1 of the second extruder directly through the material input port 2 and thereafter could thereafter likewise proceed until it reached the material input port 2 of the fourth extruder.

Five parts by weight of calcium sulfite and 50 parts by weight of water were added relative to 100 parts by weight of a corncob meal, and were inputted through its material input port 2 into the cylinder 1 of the pressure-sealed extruder as shown in FIG. 1. Then, the temperature and pressure of the first extruder were set to the values stated in Table 1, the motor was driven to rotate the screw 3 and after five minutes of kneading (steaming), a knealed product was extruded through the discharging port 11. The kneaded product extruded through the discharging port 11 was inputted directly into the cylinder 1 of the second extruder through its material input port 2, and kneading (steaming) was likewise repeated to the fourth extruder. The conditions set and kneading (steaming) time for each extruder are as shown in Table 1. The temperature and pressure stated in Table 1 are the values as determined by the temperature sensor 13 and the pressure sensor 14, respectively.

TABLE 1

|  | First extruder | Second extruder | Third extruder | Fourth extruder |
| --- | --- | --- | --- | --- |
| Temperature (° C.) | 100 | 150 | 200 | 220 |
| Pressure (MPa) | 3.5 | 10 | 22 | 28 |
| Time for treatment (min) | 5 | 5 | 5 | 15 |

The corncob meal which had been steamed by the four serially connected extruders was filtered by a filtering device, the resulting solid (cellulose) was inputted into a pressure vessel equipped with a stirrer and after was 5 parts by weight of acetic acid, 10 parts by weight of acetic anhydride and 5 parts by weight of sulfuric acid for 100 parts by weight of solid were further inputted into the pressure vessel, the mixture was reacted for 24 hours at a pressure of 10 MPa and a stirring speed of 60 rpm to yield cellulose acetate. The physical properties of cellulose acetate obtained are shown in Table 2.

TABLE 2

| Outward shape | White flaky powder |
| --- | --- |
| Specific gravity | 1.33 (25° C.), 1.36 (4° C.) |
| Bulk density (Kg/L) | 0.25–0.5 |
| Glass transition temperature (° C.) | 160–180° C. |
| Melting point (° C.) | 230–300° C. |

The filtrate from which the solid had been removed by the filtration of the steamed corncob meal by the filtering device was inputted into a reaction vessel equipped with a stirrer and having a temperature holding mechanism. After 3 parts by weight of xylanase and 0.1 part by weight of sodium hydroxide for 100 parts by weight of filtrate were inputted into the reaction vessel, the mixture was reacted for 24 hours at a temperature of 45° C. and a stirring speed of 150 rpm to yield xyloligosaccharides.

The steaming treatment of corncob meal according to the present invention has made it possible to carry out in a single step the removal of lignin from lignocelluloses which has hitherto required a lot of steps, and acetylate cellulose without conducting any pre-treatment after the removal of lignin therefrom, such as dipping the lignocelluroses in acetic acid, to thereby obtain cellulose acetate with a drastic reduction of the steps as hitherto required. It has also been possible to obtain xyloligosaccharides from the soluble xylan treatment (which has hitherto been thrown away) produced by the steaming, resulting in a conversion of at least 95% by mass of the corncob meal into products. This has made it possible to lower the cost of manufacturing cellulose acetate further, since xyloligosaccharides can be used as sweetening agents.

The present invention is an inexpensive process for manufacturing cellulose acetate useful as a biodegradable plastic by using as a raw material a corncob meal which has hitherto been thrown away. Moreover, it can provide a process for manufacturing xyloligosaccharides useful as sweetening agents from a by-product occurring from the above manufacture of cellulose acetate.

What is claimed is:

1. A process for manufacturing cellulose acetate, comprising the steps of:
    steaming a corncob meal in a sub-critical state at a temperature of 150 to 250° C. and a pressure of 20 to 29 MPa for 10 to 30 minutes to obtain a mixture of a solid product and a solution product, said solid product comprised of cellulose, said solution product comprised of soluble hemicelluloses and polyphenol converted from lignin separated from lignocelluloses in the corncob, said sub-critical state being such that the solid product and the solution product are obtained from the corncob meal solely due to the temperature and pressure conditions of the state;
    filtering the mixture to separate the solid product;
    dehydrating the solid product; and
    acetylating the dehydrated solid product in the presence of acetic anhydride and sulfuric acid to obtain cellulose acetate from the solid product.

2. The process according to claim 1, wherein the steaming is carried out in a pressure vessel and the filtering is carried out by a filtering device.

3. The process according to claim 1, wherein the steaming is carried out at a temperature of 180 to 200° C. and a pressure of 25 to 28 MPa.

4. The process according to claim 1, wherein, in the steaming step, 10 to 1000 parts by weight of water is added relative to 100 parts by weight of corncob meal.

5. The process according to claim 1, wherein, in the steaming step, a sulfurous acid compound is added to the corncob meal.

6. The process according to claim 5, wherein the sulfurous acid compound is added in the amount of 1 to 10 parts by weight for 100 parts by weight of the corncob meal.

7. The process according to claim 5, wherein, in the dehydrating and acetylating step, the sulfuric acid is added in the amount of 1 to 10 parts by weight, and the acetic anhydride is added in the amount of 1 to 20 parts by weight, relative to 100 parts by weight of dry cellulose.

8. The process according to claim 1, wherein the dehydrating and acetylating is carried out under conditions of a pressure of 5 to 15 MPa, a temperature of 60 to 100° C., a stirring speed of 30 to 100 rpm and a treatment time of 15 to 30 hours.

9. A process for manufacturing cellulose acetate, comprising the steps of:
    steaming a corncob meal at a temperature of 150 to 250° C. and a pressure of 20 to 29 MPa;
    filtering the mixture to separate the solid product;
    dehydrating the solid product; and
    acetylating the dehydrated solid product in the presence of acetic anhydride and sulfuric acid at a temperature of 60 to 100° C. and a pressure of 5 to 15 MPa for 15 to 30 hours as a single process to obtain cellulose acetate from the solid product.

10. A process for manufacturing xyloligosaccharides, comprising:
    steaming a corncob meal under conditions of a temperature of 150 to 250° C. and a pressure of 20 to 29 MPa;
    filtering the steamed corncob meal to obtain a filtrate from which solid has been removed;
    performing an enzyme treatment by reacting xylanase with soluble xylan in the filtrate to hydrolyze the soluble xylan;
    removing any suspended matter from a reaction product obtained during the enzyme treatment; and
    drying the reaction product.

11. The process according to claim 10, wherein the steaming is carried out in a pressure vessel and the filtering is carried out by a filtering device.

12. The process according to claim 10, wherein the steaming is carried out under conditions of a temperature of 180 to 200° C. and a pressure of 25 to 28 MPa.

13. The process according to claim 10, wherein, in the steaming, 10 to 1000 parts by weight of water is added relative to 100 parts by weight of corncob meal.

14. The process according to claim 10, wherein the steaming is carried out for 10 to 30 minutes.

15. The process according to claim 10, wherein, in the steaming, a sulfurous acid compound is added to the corncob meal.

16. The process according to claim 15, wherein the sulfurous acid compound is added in the amount of 1 to 10 parts by weight for 100 parts by weight of the corncob meal.

17. The process according to claim 10, wherein the xylanase is added in the amount of 0.1 to 5 parts by weight relative to 100 parts by weight of the filtrate.

18. The process according to claim 10, wherein the enzyme treatment is carried out under conditions of a pH of 3 to 8, a temperature of 30 to 50° C., a stirring speed of 60 to 200 rpm and a treatment time of 15 to 30 hours.

19. The process according to claim 10, wherein the steaming is performed by two or more sequentially connected extruders having pressure-sealed cylinders; the levels of temperature and pressure set rise gradually, beginning with the first connected extruder until the last connected extruder; and the steaming conditions for the last connected extruder satisfy the conditions of a temperature of 150 to 250° C. and a pressure of 20 to 29 MPa.

* * * * *

UNITED STATES PATENT AND TRADEMARK OFFICE
CERTIFICATE OF CORRECTION

PATENT NO. : 6,984,731 B1  
APPLICATION NO. : 10/439809  
DATED : January 10, 2006  
INVENTOR(S) : Shunichi Matsuo et al.

It is certified that error appears in the above-identified patent and that said Letters Patent is hereby corrected as shown below:

On the title page, Item [56] Column 2, FOREIGN PATENT DOCUMENTS after "3/2002" insert --D21C/05/00--.

On the title page, Column 2, Primary Examiner, delete "James D. Wilson" and insert --James O. Wilson--, therefor.

Column 1/line 35, delete "polycaplolactone" and insert --polycaprolactone--, therefore.

Column1/line 37, delete "polycaplolactone" and insert --polycaprolactone--, therefore.

Column6/line 20, delete "knealed" and insert --kneaded--, therefore.

Signed and Sealed this

Twenty-second Day of August, 2006

JON W. DUDAS  
*Director of the United States Patent and Trademark Office*